(12) United States Patent
Perez-Soler et al.

(10) Patent No.: US 7,157,098 B1
(45) Date of Patent: Jan. 2, 2007

(54) GENE THERAPY OF TUMORS USING NON-VIRAL DELIVERY SYSTEM

(76) Inventors: Roman Perez-Soler, 564 First Ave., Apt. 20T, New York, NY (US) 10016; Yiyu Zou, 8814 Ilona Ln., Apt. 2, Houston, TX (US) 77025

( * ) Notice: Subject to any disclaimer, the term of this patent is extended or adjusted under 35 U.S.C. 154(b) by 0 days.

(21) Appl. No.: 09/225,699

(22) Filed: Jan. 6, 1999

Related U.S. Application Data

(60) Provisional application No. 60/070,570, filed on Jan. 6, 1998.

(51) Int. Cl.
*A61K 51/00* (2006.01)
*A61K 9/127* (2006.01)
*C12N 15/88* (2006.01)

(52) U.S. Cl. .................. 424/450; 424/1.21; 435/458

(58) Field of Classification Search ............... 424/450; 435/320.1, 455, 458; 514/44
See application file for complete search history.

(56) References Cited

U.S. PATENT DOCUMENTS

| | | | |
|---|---|---|---|
| 5,641,662 A * | 6/1997 | Debs et al. ............... 435/172.1 |
| 5,770,222 A * | 6/1998 | Unger et al. ................ 424/450 |
| 5,795,587 A * | 8/1998 | Gao et al. .................... 424/450 |
| 5,811,406 A * | 9/1998 | Szoka, Jr. et al. ............ 514/44 |
| 5,827,703 A * | 10/1998 | Debs et al. ................. 435/455 |
| 5,837,283 A * | 11/1998 | McDonald et al. ......... 424/450 |
| 5,843,773 A * | 12/1998 | Shin et al. ............... 435/320.1 |
| 5,928,884 A * | 7/1999 | Croce et al. ............... 435/7.23 |
| 5,932,241 A * | 8/1999 | Gorman ..................... 424/450 |
| 5,998,583 A * | 12/1999 | Korsmeyer ................ 530/350 |
| 6,022,874 A * | 2/2000 | Wheeler ..................... 514/247 |
| 6,080,728 A * | 6/2000 | Mixson ....................... 514/44 |
| 6,106,859 A * | 8/2000 | Densmore, Jr. et al. .... 424/450 |
| 6,120,799 A * | 9/2000 | McDonald et al. ......... 424/450 |
| 6,193,998 B1 * | 2/2001 | Ye et al. ..................... 424/450 |

* cited by examiner

*Primary Examiner*—Janet L. Epps-Ford
(74) *Attorney, Agent, or Firm*—Benjamin Aaron Adler

(57) ABSTRACT

The present invention provides a pharmaceutical composition, comprising: (a) cationic lipids, wherein said lipids are a liposomal mixture of a diacyl-ethyl-phosphocholine and 1,2-diacyl-sn-glycero-3-phosphoethanolamine; and (b) a plasmid cDNA sequence encoding a protein having tumor suppressor or pro-apoptotic activity. This composition has a high gene transfection efficiency at non-toxic doses and is designed to transfect human bronchial premalignant lesions and early endo-bronchial malignancies. Also provided is a method of method of treating a cancerous or pre-cancerous condition of the respiratory tract in an individual in need of such treatment, comprising the step of administering to said individual a pharmacologically effective dose of a pharmaceutical composition, comprising: (a) cationic lipids, wherein said lipids are a liposomal mixture of a diacyl-ethyl-phosphocholine and 1,2-diacyl-sn-glycero-3-phosphoethanolamine; and (b) a plasmid cDNA sequence encoding a protein having tumor suppressor or pro-apoptotic activity.

6 Claims, 8 Drawing Sheets

SEQUENCE LISTING

```
<160> NUMBER OF SEQ ID NOS: 3

<210> SEQ ID NO 1
<211> LENGTH: 12
<212> TYPE: DNA
<213> ORGANISM: artificial sequence
<220> FEATURE:
<221> NAME/KEY: primer_bind
<223> OTHER INFORMATION: RT-1 primer used for human p53 cDNA

<400> SEQUENCE: 1
cgggaggtag ac                                                       12

<210> SEQ ID NO 2
<211> LENGTH: 31
<212> TYPE: DNA
<213> ORGANISM: artificial sequence
<220> FEATURE:
<221> NAME/KEY: primer_bind
<223> OTHER INFORMATION: human p53 -specific primer P3

<400> SEQUENCE: 2
atttgatgct gtccccggag gatattgaas c                                  31

<210> SEQ ID NO 3
<211> LENGTH: 31
<212> TYPE: DNA
<213> ORGANISM: artificial sequence
<220> FEATURE:
<221> NAME/KEY: primer_bind
<223> OTHER INFORMATION: human p53 -specific primer P4

<400> SEQUENCE: 3 acccttttg gacttcaggt ggctggagts g                                   31
```

GENE THERAPY OF TUMORS USING NON-VIRAL DELIVERY SYSTEM

This application claims the benefit of Provisional Application No. 60/070,570 filed Jan. 6, 1998.

FEDERAL FUNDING LEGEND

The present invention was created in part using federal funds under NIH grant CA 50270. Accordingly, the U.S. government has certain rights in this invention.

BACKGROUND OF THE INVENTION

1. Field of the Invention

The present invention relates generally to the fields of gene therapy and cancer therapeutics. More specifically, the present invention relates to a gene therapy of lung tumors and lung premalignancy using a non-viral delivery system.

2. Description of the Related Art

Lung cancer is the leading cause of cancer-related death. It has a nearly 90% mortality with a median patient survival of less than 2 years (D. J. Minna, *Adv. in Oncology.* 12, 3–8 (1996)). In 1997, it was estimated that a total of 178,100 new patients were diagnosed in the US, and 160,400 died of the disease (S. L. Parker, T. Tong, S. Bolden, P. A. Wingo, *CA Cancer J Clin* 47: 5–27 (1997)). The major reasons for such dismal prognosis are the lack of effective preventive interventions and therapies for advanced disease. In most cases of clinically diagnosed lung cancer, malignant cells have already spread into lung parenchyma, regional lymph nodes, and/or extrathoracic organs.

Lung cancer arises in a diffusely damaged bronchial epithelium and is preceded by recognizable histological changes. The earliest changes include squamous metaplasia, followed by three grades of dysplasia, carcinoma in situ, microinvasive cancer, and invasive cancer (W. P. Bennett et al., *Cancer Res.* 53, 4817–4822 (1993)). From a clinical point of view, the best approach to reduce lung cancer mortality may be to effectively identify and treat bronchial malignancies before they become invasive.

Lung cancers are the result of mutations accumulated during a person's life. By the time lung cancer manifests itself clinically, there may be 10 or 20 such accumulated mutations in the lung cancer cells. The loss of function of tumor suppressor genes and the activation of dominant oncogenes play crucial roles in the pathogenesis of lung cancer. Particularly, p53 alterations occur in 30–60% of premalignant bronchial dysplasias and 60–70% of lung carcinomas (W. P. Bennett et al., *Cancer Res.* 53, 4817–4822 (1993)). Over-expression of p53 can induce growth arrest or apoptosis in many types of cancer cells (A. J. Levine, *Cell* 88, 323–331 (1997), S. W. Lower, *Curr. Opin. Oncol.* 7, 547–553 (1995); U. Tormanen et al., *Cancer Res.* 55, 5595–5602 (1995); Reeve, et al. *British J. Cancer.* 73,1193–1200 (1996)). These characteristics make p53 a target for lung cancer gene therapy.

Prior gene therapy studies in lung cancer used viral vectors and direct tumor inoculation. Viruses are more efficient than liposomes in transfecting cells but are also more toxic and immunogenic. As a result, repeated administration is unrealistic. In addition, aerosolization of viral preparations may result in infection of healthy individuals if not performed in an isolated area.

The prior art is deficient in the lack of effective means of treating lung cancer. The present invention fulfills this longstanding need and desire in the art.

SUMMARY OF THE INVENTION

To reduce lung cancer mortality, an approach to effectively treat bronchial premalignancy and early bronchial malignancy before it becomes invasive was developed. A non-viral system to deliver different genes locally to kill malignant cells in the bronchial epithelium was developed. A mouse tumor model mimicking early human bronchial malignancy was created to illustrate this system in vivo. The p53 gene was successfully delivered into and effectively killed human lung cancer cells in mouse bronchial epithelium. Tumor formation was reduced significantly and the life span of treated mice more than doubled. These results have important implications for the gene therapy and prevention of human lung cancer.

In one embodiment of the present invention, there is provided a pharmaceutical composition, comprising: (a) cationic lipids, wherein said lipids are a liposomal mixture of a diacyl-ethyl-phosphocholine and 1,2-diacyl-sn-glycero-3-phosphoethanolamine; and (b) a plasmid cDNA sequence encoding a protein having tumor suppressor or pro-apoptotic activity.

In another embodiment of the present invention, there is provided a method of treating a cancerous or pre-cancerous condition of the bronchial epithelium of the respiratory tract in an individual in need of such treatment, comprising the step of administering to said individual a pharmacologically effective dose of a pharmaceutical composition, comprising: (a) cationic lipids, wherein said lipids are a liposomal mixture of a diacyl-ethyl-phosphocholine and 1,2-diacyl-sn-glycero-3-phosphoethanolamine; and (b) a plasmid cDNA sequence encoding a protein having tumor suppressor or pro-apoptotic activity.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
FIG. 1 shows the expression of p53 protein in H358 cells transfected with DP3/p53 complexes. Western blot confirming wild-type p53 expression in H358 cells transfected with DP3/p53 at different time points. First row, lanes 1 to 8 represent samples transfected with DP3/p53 at time point 0, 3, 6, 12, 24, 36, 48, and 72 hours after transfection was started, respectively. The second row is actin control.

The present invention is directed to a non toxic, non-immunogenic, cationic lipid formulation that can be used to transfect specific genes in bronchial epithelium by aerosolization. This invention may be used to correct genetic defects in premalignant lesions in the bronchial epithelium of patients at risk for lung cancer and thus delay or prevent lung cancer.

Thus, the present invention provides a pharmaceutical composition, comprising: (a) cationic lipids, wherein said lipids are a liposomal mixture of a diacyl-ethyl-phosphocholine and 1,2-diacyl-sn-glycero-3-phosphoethanolamine; and (b) a plasmid cDNA sequence encoding a protein having tumor suppressor or pro-apoptotic activity. Preferably, the diacyl-ethyl-phosphocholine is selected from the group consisting of dipalmytoyl ethylphosphocholine (DPEP), dimyristoyl ethylphosphocholine (DMEP) and dilauroyl ethylphosphocholine (DLEP). Generally, the lipid ratio of diacyl-ethyl-phosphocholine to DOPE is from about 6:1 to about 1:1. Preferably, the liposomal mixture has a size of from about 25 nm to about 1,500 nm. More preferably, the liposomal mixture has a size of from about 100 nm to about 500 nm. Although other genes may be useful in the composition of the present invention, representative examples of proteins having tumor suppressor activity include p53, p16, retinoblastoma and fragile hystidine triad gene (FHIT), Negrini et al., *Cancer Research*, 56(14): 3173–9, 1996 Jul. 15. Representative examples of proteins with pro-apoptotic activity are bax, bak and bad.

The present invention is also directed to a method of treating a cancerous or pre-cancerous condition of the bronchial epithelium of the respiratory tract in an individual in need of such treatment, comprising the step of administering to said individual a pharmacologically effective dose of a pharmaceutical composition, comprising: (a) cationic lipids, wherein said lipids are a liposomal mixture of a diacyl-ethyl-phosphocholine and 1,2-diacyl-sn-glycero-3-phosphoethanolamine; and (b) a plasmid cDNA sequence encoding a protein having tumor suppressor or pro-apoptotic activity. Preferably, the diacyl-ethyl-phosphocholine is selected from the group consisting of dipalmytoyl ethylphosphocholine (DPEP), dimyristoyl ethylphosphocholine (DMEP) and dilauroyl ethylphosphocholine. Generally, the lipid ratio of diacyl-ethyl-phosphocholine to DOPE is from about 6:1 to about 1:1. Preferably, the liposomal mixture has a size of from about 25 nm to about 1,500 nm. More preferably, the liposomal mixture has a size of from about 100 nm to about 500 nm. Although other genes may be useful in the composition of the present invention, representative examples of proteins having tumor suppressor activity include p53, p16, retinoblastoma and FHIT. A representative example of a protein with pro-apoptotic activity is bax.

In one embodiment, the composition of the present invention is administered to the lower respiratory tract intratracheally. Alternatively, the composition is administered to the lower respiratory tract by aerosolization. Preferably, the composition is administered to the individual in a dose of from about 0.01:0.06 mg/kg of the DNA: lipid composition to about 10:60 mg/kg of the DNA:lipid composition. Preferably, the lipid:DNA ratio of the composition of the present invention is about 2:1 to about 24:1.

It is specifically contemplated that kits may be prepared using the novel lipid formulations of the p53 gene or other genes as described by the present invention. In such a case, the lipid composition and therapeutic genes would be stored as solids in separate vials prior to reconstitution. Upon reconstitution, the solution is aerosolized using a nebulizer machine. A person having ordinary skill in this art would readily be able to determine, without undue experimentation, the appropriate dosages and routes of administration of the novel protein of the present invention.

The following examples are given for the purpose of illustrating various embodiments of the invention and are not meant to limit the present invention in any fashion.

The present invention discloses a cationic liposome gene delivery system intended for aerosol administration to treat bronchial premalignancy and malignancy. Various liposome/DNA formulations using different cationic lipids, liposome sizes, lipid/DNA ratios, and DNA doses were tested in six human cancer cell lines and normal bronchial epithelial cells to screen for high transfection efficiency and low toxicity. DP3 liposome was chosen to form liposome/DNA complex (DP3/p53) with a human wild-type p53 expression plasmid (pC53SN) based upon its relatively high transfection efficiency and low toxicity compared with other cationic liposome formulations.

In the preparation of different liposome formulations composed of cationic lipids, a wide variety of different lipid composition were used to prepared different liposome-DNA preparations using the Lac Z gene. All preparation obtained with commercially available individual cationic lipids were prepared by thin layer hydration or detergent removal method. The final total lipid concentration was 2 mg/ml.

The following preparations were made available in a ready to use form. Lipofectamine ($L_f$) was purchased from Gibco, $L_v$ was provided by Vical and G53 and G 67 by Genzyme corporation. The final lipid concentration of these formulations was 1 mg/ml, 2 mg/ml, and 1.3 mg/ml, respectively. The liposome particle size was measured by Nicomp Submicron Particle Sizer 370. The characteristics of all formulations tested is shown below.

TABLE I

Characteristics of Lipsome Formulations

| Name (nm) | Composition | Lipid ration (mol) | Size |
|---|---|---|---|
| L1 | DODAP/DOPE | 3:1 | 78.3 ± 45.2 |
| L2 | DODAP/DOPE | 1:1 | 88.6 ± 42.1 |
| L3 | DODAP/DOPE | 1:3 | 83.6 ± 37.8 |
| L4 | DOTAP/DOPE | 3:1 | 59.2 ± 33.9 |
| L5 | DOTAP/DOPE | 1:1 | 66.9 ± 34.9 |
| L6 | DOTAP/DOPE | 1:3 | 70.9 ± 38.1 |
| DL2 | DLEP/DOPE | 2:1 | 230 ± 175 |
| DL3 | DLEP/DOPE | 3:1 | 146 ± 85 |
| DM2 | DMEP/DOPE | 2:1 | 1000; 80 |
| DM3 | DMEP/DOPE | 3:1 | 1250; 39 |
| DP2 | DPEP/DOPE | 2:1 | 1250; 155 |
| DP3 | DPEP/DOPE | 3:1 | 80.0 ± 25.2 |
| other sources | | | |
| $L_f$/Gibco | DOSPA/DOPE | 3:1 | 79.8 ± 54.5 |
| $L_v$/Vical | DMRIE/DOPE | 1:1 | 1148 ± 683 |
| G53/Gen | L#53/DOPE | 1:2 | 420 ± 314 |
| G67/Gen | L#67/DOPE | 1:2 | 380 ± 280 |

In Vitro Transfection Efficiency (Lac Z Gene)

These initial studies were performed using NIH3T3 cells and the Lac Z gene. 3–5×10⁵ NIH3T3 cells/well were plated in 6 well dishes. Liposome-pCMV-β-gal(Lac Z) complexes in a serum-free medium were added to the wells and the cells were incubated at 37° C. with 5% $CO_2$ air for 24 hours. Subsequently, the liposome-DNA complexes were washed out and medium supplemented with 10% FBS added. The β-galactosidase activity was determined at 24 hours post-incubation by x-gal staining (54); 6 different fields were randomly selected with at least 200 cells in each field. % transfection was expressed as the percent of blue-stained cells.

TABLE II shows the transfection efficiency is highly dependent on the lipid composition. The highest % transfection was consistently observed with Lf, followed by DP3.

TABLE II

| Formulation | % Transfection | Number of exp. |
|---|---|---|
| DP3 | 11.2 ± 6.6 | 4 |
| Lf | 17.4 ± 8.4 | 10 |
| G67 | 8.5 ± 2.1 | 4 |
| L1 | 0.2 ± 0.3 | 3 |
| L2 | 0.3 ± 0.2 | 3 |
| L3 | 0.6 ± 0.3 | 3 |
| L4 | 1.7 ± 0.4 | 3 |
| L5 | 5.4 ± 1.1 | 3 |
| L6 | 5.6 ± 1.0 | 3 |
| DL2 | 3.8 ± 1.5 | 3 |
| DL3 | 4.7 ± 1.4 | 3 |
| DM2 | 4.2 ± 1.2 | 3 |
| DM3 | 11.4 ± 5.2 | 4 |
| DP2 | 3.1 ± 0.9 | 3 |
| $L_v$ | 2.3 ± 1.2 | 8 |
| G53 | 6.2 ± 1.4 | 3 |

Effect of Lipid: DNA Ratio on Transfection Efficiency (Lac Z Gene)

The experimental conditions were the same as for the experiments shown above. The DNA amount was fixed at 2 µg/well. Different lipid:DNA weight rations (1:1, 2:1, 3:1, 6:1, 12:1, and 24:1) were used. % transfection with each lipid:DNA ratio was calculated using the method described above. The experiments performed twice. TABLE III shows that the transfection efficiency can be optimized by altering the lipid:DNA ratio. The optimal lipid:DNA ratio varies amount the different formulations.

TABLE III

| Formulation | % Transfection lipid:DNA ratio | | | | | |
|---|---|---|---|---|---|---|
| | 1:1 | 2:1 | 3:1 | 6:1 | 12:1 | 24:1 |
| $L_f$ | — | 0 | 2 | 6 | 23 | 8 |
| DP3 | — | 2 | 5 | 9 | 14 | 10 |
| DM3 | — | — | 5 | 11 | 15 | 1 |
| L5 | — | — | 0.5 | 4 | 7 | — |
| L6 | — | — | 0.3 | 3 | 7 | — |
| $L_v$ | — | — | 2 | 2 | 1 | — |
| G53 | 4 | 5 | 3 | 1 | — | — |
| G67 | 7 | 9 | 4 | 2 | — | — |

Effect of Liposome Size on Transfection Efficiency (Lac Z Gene)

The experimental design was as described above. Liposomes of different size were prepared and purified by extrusion, sonication, and centrifugation methods. The sizes in the table below represent the size range of >98% particles measured with Nicomp Submicron Particle Sizer 370. % transfection data are mean±SD of 3 different experiments. TABLE IV shows that the highest transfection efficiency was obtained by using liposomes ranging between 60 and 110 nm in median size.

TABLE IV

| Formulation | % Transfection Size (nm) | | | | |
|---|---|---|---|---|---|
| | 1200–80 | 550–400 | 240–170 | 110–60 | 40–20 |
| DP3 | 0.9 ± 0.5 | 2.1 ± 0.4 | 4.1 ± 0.7 | 10.6 ± 1.2 | 8.5 ± 1.1 |
| DM3 | 0.8 ± 0.4 | 4.2 ± 1.0 | 5.9 ± 1.2 | 11.2 ± 1.7 | 7.6 ± 1.1 |
| L5 | 1.1 ± 0.5 | 2.0 ± 0.5 | 2.4 ± 0.6 | 5.7 ± 0.9 | 5.4 ± 0.7 |
| L6 | 0.3 ± 0.1 | 1.8 ± 0.2 | 2.3 ± 0.2 | 6.1 ± 0.4 | 6.2 ± 0.4 |
| G53 | 1.2 ± 0.6 | 1.8 ± 0.7 | — | 7.8 ± 2.4 | 7.3 ± 2.1 |
| G67 | 1.4 ± 0.7 | 1.6 ± 0.5 | 2.8 ± 0.8 | 9.2 ± 2.2 | 8.5 ± 1.9 |
| Lv | 0.1 ± 0.2 | 0.6 ± 0.4 | 1.2 ± 0.5 | 2.6 ± 0.8 | 2.8 ± 0.9 |

Effect of Cell Type on Transfection Efficiency (Lac Z Gene)

The optimal lipid:DNA ratio and size selected from previous above experiments were used. Experiments were repeated 3 to 5 times. The data are mean±SD. TABLE V shows that the transfection efficiency is cell-line dependent. Lf was the best formulation and Dp3 was the second best in 4 of the 5 cell lines tested.

TABLE V

| | % Transfection | | | |
|---|---|---|---|---|
| | | | | Cells |
| Formulation | 3T3 | Broncial | SAOS2 | A549H358 |
| DP3 | 13.8 ± 3.4 | 9.4 ± 2.3 | 4.7 ± 1.4 | 3.9 ± 1.5 | 10.7 ± 3.6 |
| L6 | 6.1 ± 0.4 | 5.1 ± 1.7 | 5.5 ± 2.1 | 2.0 ± 0.8 | 1.7 ± 1.1 |
| $L_f$ | 19.4 ± 4.5 | 11.7 ± 3.2 | 16.7 ± 4.2 | 12.1 ± 3.5 | 11.2 ± 3.7 |
| $L_v$ | 2.8 ± 0.9 | 2.1 ± 1.3 | 3.5 ± 1.6 | 0.9 ± 0.7 | 4.2 ± 1.3 |

Lipid Toxicity

The toxicity of the DP3 and the liposomes was tested in 3T3 cells. In these experiments, DP3 was much less cytotoxic per se to cells. Therefore, from all formulations tested, DP3 had the best percentage transfection efficiency with the highest non-toxic dose.

In Vitro Transfection of the p53 Gene by Analysis of p53 Function

The following formulations were selected for studies with the p53 gene: Lf, DP3, G53, and G67 using the optimal particle size and lipid:DNA ratio. Two cell lines with no p53 expression (SAOS-2 and H358) were used. To analyze the p53 function in the transfected cells, the cells were co-transfected with liposome-p53 or liposome-irrelevant plasmid (empty vector) complexes (DNA dose 5 µg), the wwp-Luc plasmid which contains the luciferase gene under the control of the p21 promoter (gift from Dr. Bert Vogelstein) and the Lac Z gene. The duration of transfection was 24 hours. After transfection, the cells were lysed and the luciferase activity was determined by luminometry. If the p53 gene was successfully transfected and translated, there is induction of 21 and consequently induction of luciferase. p53 function is, therefore, directly proportional to luciferase activity measured by luminometry. β-galactosidase activity was measured as described. To correct for background and transfection efficiency, the relative p53 activity was established.

$$\frac{\text{(luciferase activity in } p53 \text{ transfected cells:}}{\beta\text{-gal activity in } p53 \text{ transfected cells)}}$$
$$\overline{\text{(luciferase activity in cells transfected with irrelevant plasmid:}}$$
$$\beta\text{-gal activity in cells transfected with irrelevant plasmid)}$$

The results are shown below in TABLE VI and shows that Lf and DP3 were about equally effective in inducing p53 function in transfected cells.

TABLE VI

Relative p53 activity after transfection with liposome: p53 complexes

| | Relative p53 activity | |
|---|---|---|
| | Cells | |
| Complex | SAOS-2 | H358 |
| Lf: wt-;53 | 31 ± 7 | 35 ± 9 |
| Lf: mu-p53 | 7 ± 3 | 6 ± 3 |
| $DP_3$: wt-p53 | 27 ± 6 | 29 ± 4 |
| $DP_3$: mu-p53 | 5 ± 2 | 4 ± 1 |
| G53: wt p53 | 12 ± 5 | 9 ± 3 |
| G53: mu-p53 | 5 ± 2 | 4 ± 2 |

TABLE VI-continued

Relative p53 activity after transfection with liposome: p53 complexes

| | Relative p53 activity | |
|---|---|---|
| | Cells | |
| Complex | SAOS-2 | H358 |
| G67: wt-p53 | 19 ± 6 | 24 ± 10 |
| G67: mu-p53 | 7 ± 3 | 6 ± 2 |

The optimized DP3/p53 formulation had a liposome/DNA weight ratio of 6:1. DP3, the cationic liposome prepared by hydration method followed by extrusion (0.2 µm filter), is composed of 1,2-dipalmitoyl-sn-glycero-3-ethylphosphocholine (DPEP) and dioleoyl 1,2-diacyl-sn-glycero-3-phosphoethanolamine (DOPE) at a weight ratio of 3:1 (particle size 60–110 nm). The DP3/p53 complex was formed by mixing the DP3 liposomes with pc53SN in Opti-Mem (Gibco) at a weight ratio of 6:1 and incubating at 37° C. for 20 minutes).

The delivery system was first tested in vitro in a human lung cancer cell line H358, which contains a p53 deletion. To show that H358 cells express p53 protein after DP3 liposome-mediated transfection, DP3/p53 (2 µg DNA/$10^6$ cells) was introduced into H358 cells as follows. Briefly, H358 cells ($10^6$/well) were exposed to DP3/DNA complexes (DNA dose: 2 µg/$10^6$ cells) in Opti-Mem for 6 hours and then an equal amount of RPMI 1640 (Gibco) containing 20% FBS (Gibco) was added for another 24 hours. The transfection was terminated by replacing the media with fresh RPMI containing 10% FBS. The culture condition was maintained at 37° C. and 5% $CO_2$ throughout the transfection process. Subsequently, p53 protein was detected by western blotting at different time points (FIG. 1). Relative p53 protein expression level was measured by laser scanning densitometry. p53 protein was detectable at 6 hours after transfection was started. Significant expression was observed as early as at 12 hours and the peak of expression was observed at 36 hours. By 72 hours, the level of p53 protein expression was still about 60% of the peak level.

To ascertain whether the expressed p53 protein was functional, three plasmids, pC53SN, wwp-luc (containing the luciferase gene under the control of a p21 promoter), and pCMV-β-gal (containing the LacZ gene under the control of a CMV promoter) were cotransfected into H358 and Saos2 cells with DP3 as follows. Briefly, 2×$10^6$H358 or Saos2 cells were plated in 90 mm culture dishes. After 24 hours the cells were transfected with DP3/DNA complexes containing equal amount of three plasmids of wwp-luc, pCMV-β-gal, pc53SN or vector plasmid (2 µg DNA/$10^6$ cells). The transfection process was the same as described above. Cells were incubated for 36 hours after transfection was terminated, and then washed with 4° C. PBS and harvested with a cell scraper in 1.0 ml of the luminometry reaction buffer at 4° C. Cells were resuspended carefully and the suspesion was sonicated for 2 minutes on ice and centrifuged at 1,000×g for 5 minutes. 25 µl of the supernatant was mixed with 325 µl of the reaction buffer and 100 µl of luciferin solution (0.3 mg/ml) on ice, and was measured immediately in a luminometer (TD20/20; Promega). β-galactosidase activity of 25 µl of the supernatant was measured as previously described (J. A. Roth et al., *Nat. Med.* 2, 985–991 (1996); P. L. Felgner et al., *Proc. Natl. Acad. Sci. USA.* 84, 7413–7417 (1987).

Figure 2:
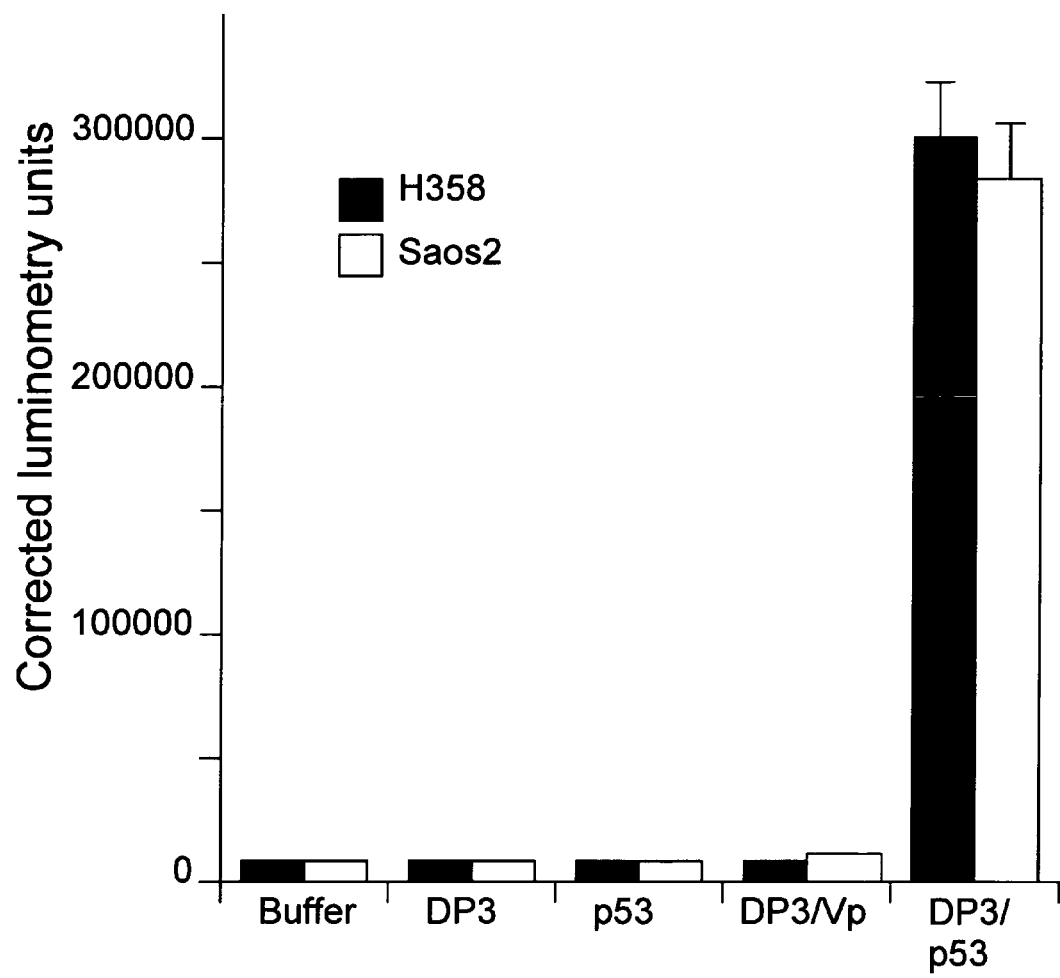
FIG. 2 shows the functional assay of p53 in H358 cells transfected with DP3/p53 complex. In the figure: Buffer, p53, DP3, DP3/Vp, and DP3/p53 represent cells treated with luminometry reaction buffer (100 mM $KH_2PO_4$, 5 mM ATP, 15 mM $MgSO_4$, 1 mM DTT, pH7.8), pC53SN alone, DP3 liposome alone, DP3/vector plasmid complex, and DP3/p53 complex, respectively. p53 function was measured by luciferase activity. Transfection efficiency was measured by β-galactosidase activity. Luminometry units were divided by OD values of b-galactosidase activity to factor out uneven transfection efficiency, and were shown here as Corrected Luminometry Units. The data represent the mean±SD of three independent experiments.

If expressed p53 is functional, it will activate the p21 promoter and induce the expression of luciferase. Luciferase and β-gal activities were measured 48 hours after the completion of transfection. Luciferase activities corrected for transfection efficiency measured by β-gal activity showed a 130-fold induction in cells transfected with DP3/p53 but no induction in cells transfected with pC53SN plasmid alone, DP3 liposome alone, or DP3/vector plasmid (FIG. 2). Thus, cells transfected with DP3/p53 express functional p53 protein.

Figure 3:
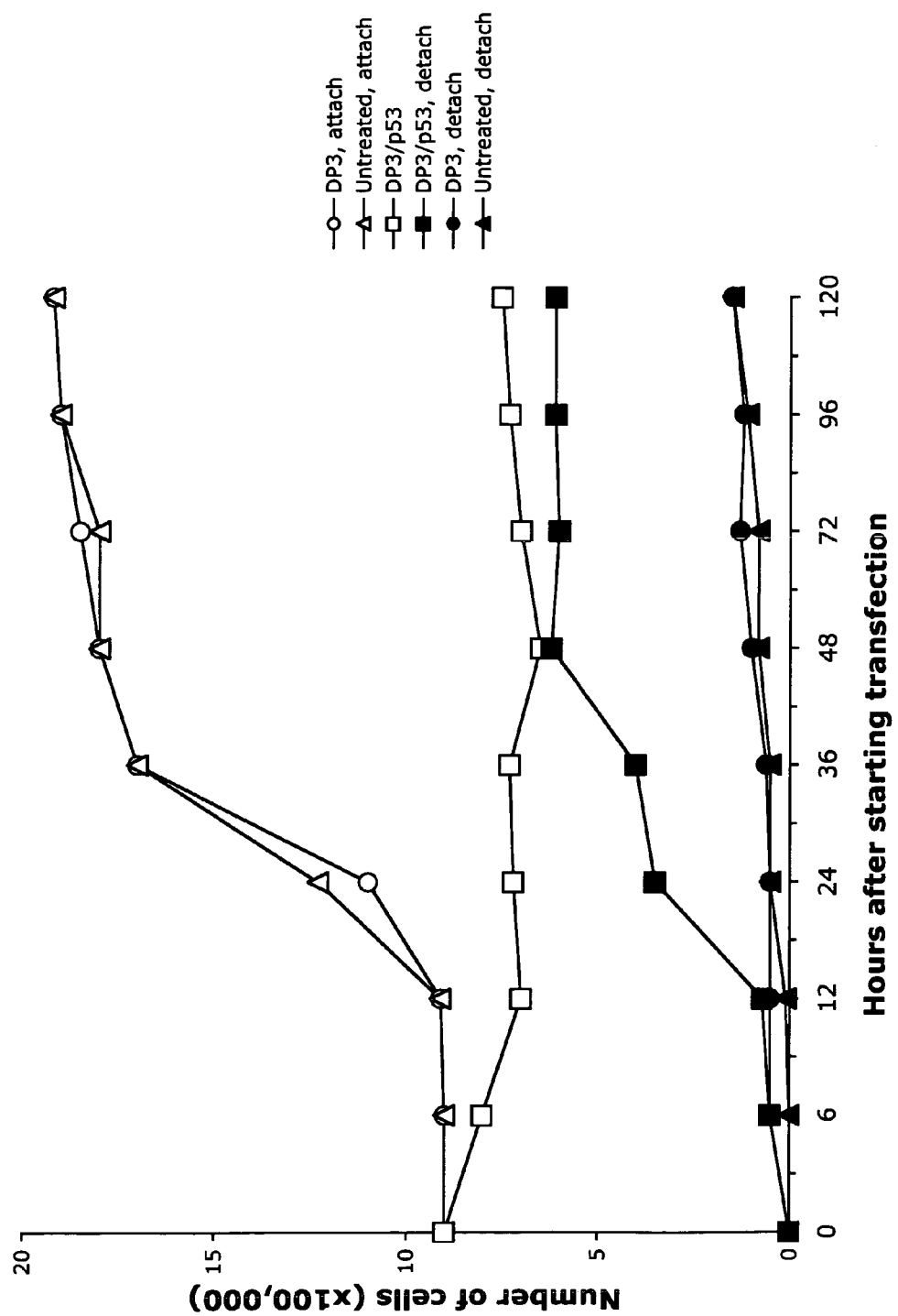
FIG. 3 shows the H358 cell growth arrest and death induced by DP3/p53 transfection. Cells were suspended in 0.2% Trypan blue solution and counted with hematometer under a microscope at indicated time points. The data represents the mean±SD of three independent experiments.

In H358 cells, the transfected p53 caused cell growth arrest and death (FIG. 3). H358 cells ($10^6$/well in 1.0 ml Opti-Mem) were plated in 6-well plates, grown for 24 hours at 37° C. and 5% $CO_2$, and then transfected with DP3/p53. Untreated H358 cells and cells exposed to DP3 alone were used as controls. Cells were trypsinized and resuspended into normal saline containing 0.2% Trypan blue and counted at 0, 6, 12, 24, 36, 48, 72, 96, and 120 hours after transfection was started.

Cultures exposed to DP3/p53 showed a flat cell growth curve with a progressive decrease in the number of attached cells and increase in the number of detached cells, with about 50% of cells detached at 48 hours after the transfection was started. Untreated cells and cells treated with DP3 alone grew exponentially for 48 hours, entered a quiescent phase, and remained attached to culture plates. Therefore, DP3 alone did not have any cell growth inhibitory effect and did not cause cell detachment. This result also showed that DP3 liposomes had no significant toxicity.

To demonstrate that cell death after DP3/p53 transfection was due to apoptosis, TUNEL assays were performed. Apoptotic cells were examined by flow cytometry. Thirty hours after DP3/p53 transfection, 85% of the detached cells and 15% of the attached cells were apoptotic cells, indicating that DP3/p53 transfection induced apoptosis in H358 cells. Apoptosis in the transfected cells was also confirmed by agarose gel electrophoresis (data not shown). DP3/p53 transfected cells showed a strong fluorescent signal indicating the presence of DNA fragmentation in the apoptotic cells (data not shown).

Figure 4:
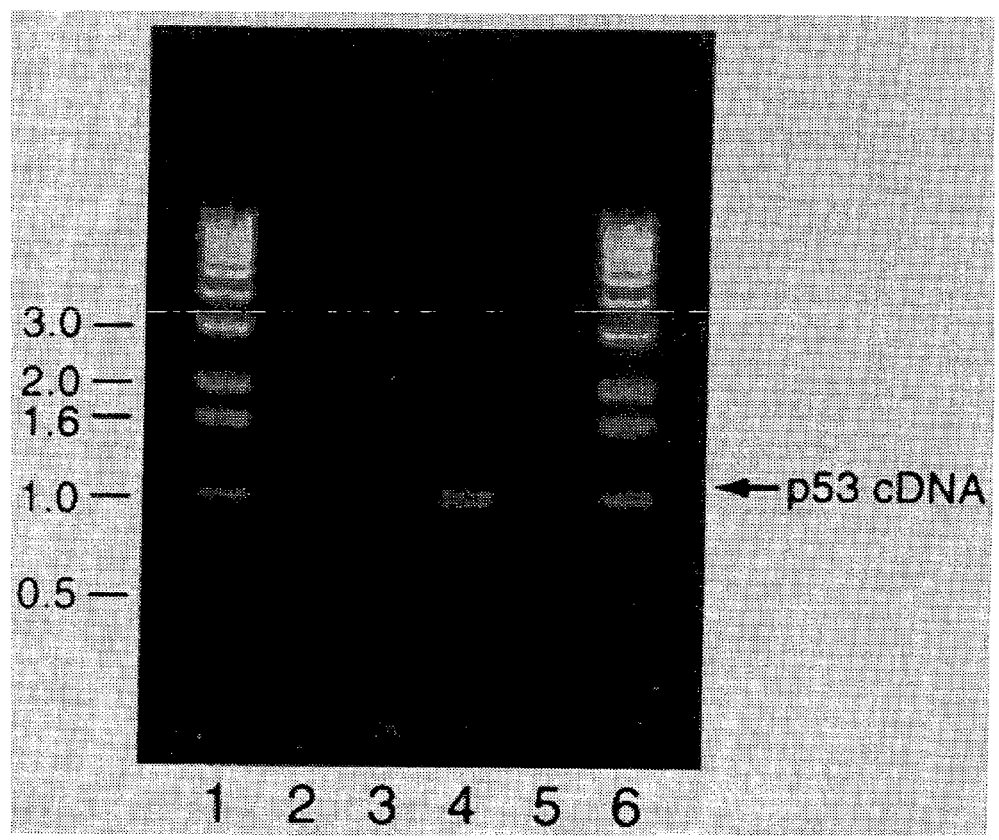
FIG. 4 shows the RT-PCR assay confirming in vivo p53 mRNA expression after intratracheal administration of DP3/p53. Lanes 1 and 6, 1 Kb DNA ladder markers. Lane 2, normal wild-type p53 mouse (C57BL/6), no treatment. Lane 3, p53 null mice (male, C57BL/6, 8 weeks old, from Taconic Quality Laboratory Animals and Services for Research) treated with DP3 alone. Lane 4, p53 null mice treated with DP3/p53. Lane 5, p53 null mice treated with DP3/p53, no reverse transcriptase.

In vivo, an RT-PCR assay was used to demonstrate that pC53SN plasmid can be delivered into bronchial epithelial cells by DP3 liposome-mediated transfection. Briefly, tissue total RNA was extracted with RNA Isolator (Genosys) and 2.3 µg from each sample used for the RT-PCR reaction. The RNA was incubated with reverse transcriptase, dNTPs, and RT-1 primer (CGGGAGGTAGAC) for 1 hour at 46° C. Then PCR components were added to the reaction mixture, including Taq polymerase (Perkin-Elmer), human-p53-specific primers (P3 primer ATTTGATGCT GTCCCCGGAG-GATATTGA A-s-C and P4 primer ACCCTTTTTGGACT-TCAGGTGGCTGGAGT-s-G) (Genosys). The mixtures were amplified in 30 PCR cycles using the following conditions: 94° C. for 30 seconds, 65° C. for 60 seconds, 78° C. for 80 seconds.

p53-null mice (C57BL/6) were treated intratracheally with DP3/p53. p53 null mice treated with DP3 alone and normal wild-type p53 mice (C57BL/6) without treatment were used as controls. The dose was 8 µg DNA/48 µg DP3/day for 4 consecutive days. Animals were sacrificed on day 5 and the lungs resected and immediately frozen in liquid nitrogen until analysis. Total tissue RNA was extracted and used for RT-PCR assays. Human-p53-specific PCR primers were used and there was a strong p53 cDNA signal in the sample treated with DP3/p53 and a much weaker signal in the same sample without reverse transcriptase added in the RT-PCR reaction, but no detectable signals in the control samples. FIG. 4 shows that the human p53 mRNA expression in the mouse lung was caused by the transfected pC53SN plasmid.

To determine the effectiveness of DP3/p53 treatment on tumor formation in vivo, a human lung cancer model in nude mice was developed that mimics human bronchial malignancy and early lung cancer. Briefly, male nu/nu mice (7–8 weeks old, 18–22 g, Harlan Sprague Dawley Inc.) were inoculated with H358 or H322 cells ($1-2\times10^6$ cells/mouse) intratracheally. Inoculated cells initially attach to the surface of the bronchial epithelium. By week 2–4, multiple microscopic tumors in the bronchial epithelium in connection with the bronchial lumen are well established. By week 7–9, animals display multiple visible bilateral lung tumor nodules. By week 10–15, animals die of multiple bilateral lung tumors without distant metastases.

Figure 5:
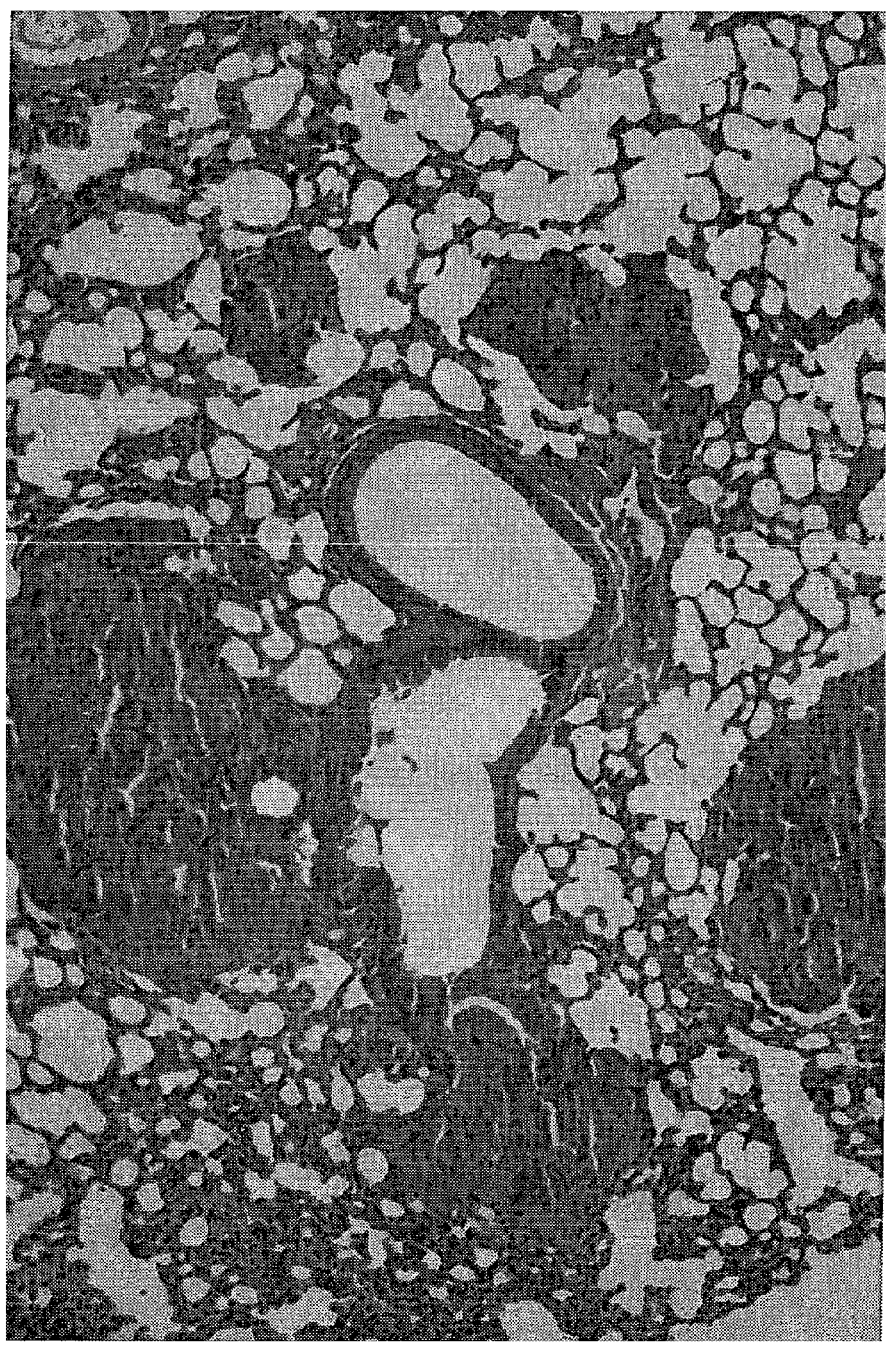
FIG. 5 mouse lung biopsy 2 weeks after intratracheal H358 tumor inoculation. Human lung cancer cells H358 (p53 gene deletion, $1-2\times10^6$/mouse) were inoculated intratracheally in nu/nu mice. (1) bronchiole, (2) H358 tumor.

Human lung cancer cells were implanted into the mouse bronchi intratracheally. These lung cancer cells attached to the bronchial epithelium and gave rise to multiple tumors and the life spans of mice correlated with the number of cancer cells inoculated. FIG. 5 shows the mouse lung biopsy 2 weeks after intratracheal H358 tumor inoculation. H358 cells grew orthotopically in the lungs of nude mice in a multinodular pattern similar to that of human bronchioalveolar carcinoma and caused animal death by local growth without evidence of metastatic spread.

Figure 6:
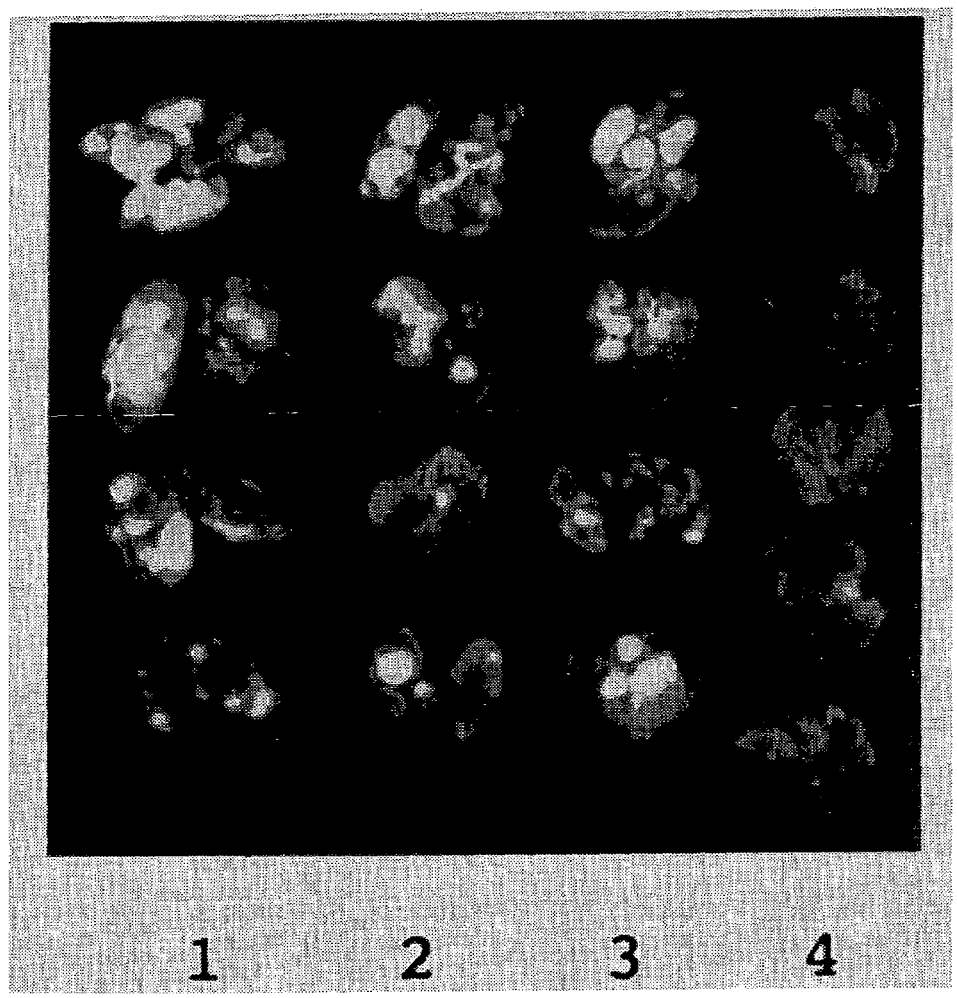
FIG. 6 shows the in vivo lung tumor growth inhibition by intratracheal administration of DP3/p53. Lane 1, untreated mice. Lane 2, mice treated with pC53SN plasmid alone. Lane 3, mice treated with DP3 liposomes alone. Lane 4, mice treated with DP3/p53 complex. The white spots in the lungs of the control groups (Lanes 1–3) are tumors. The treated lungs (Lane 4) show the characteristics of normal lungs. The experiment was repeated twice.
Figure 7A:
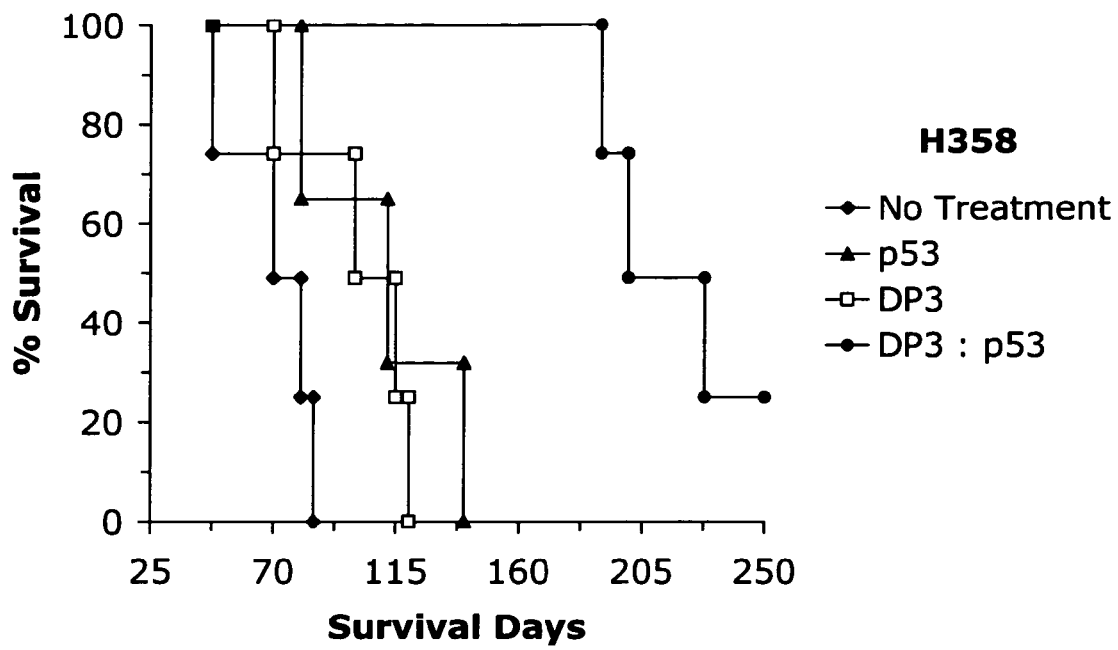
FIG. 7 shows the lung tumor bearing mouse survival test. Male nu/nu mice were inoculated intratracheally with H358 or H322 cells. The inoculated mice were divided into 4 groups with 5 mice in each for experiments 1–3 and 4 mice in each for experiment 4. In each experiment, one group was untreated, and the other three groups were administered intratracheally with pC53SN plasmid alone, DP3 liposomes alone, or DP3/p53 complex on days 4, 8, 12, 16, and 20 after H358 inoculation. Moribund mice were sacrificed and autopsied and lung tumors were found in all animals. The life spans of the animals were recorded. Differences in survival between groups were analyzed for statistical significance using a Log rank test.
Figure 7B:
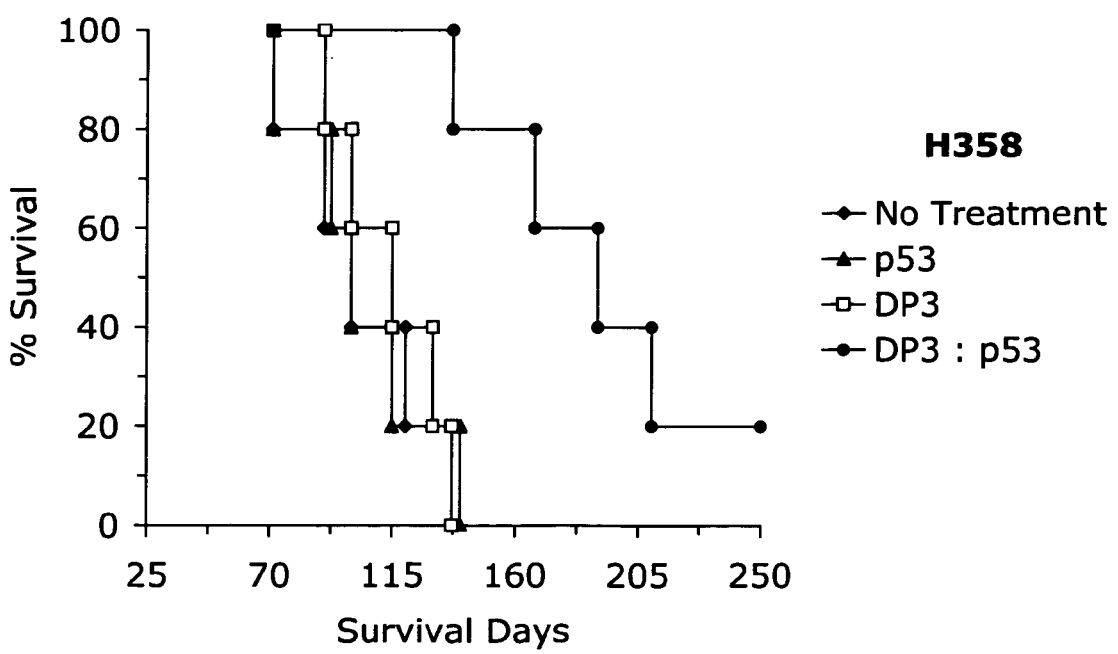
Figure 7C:
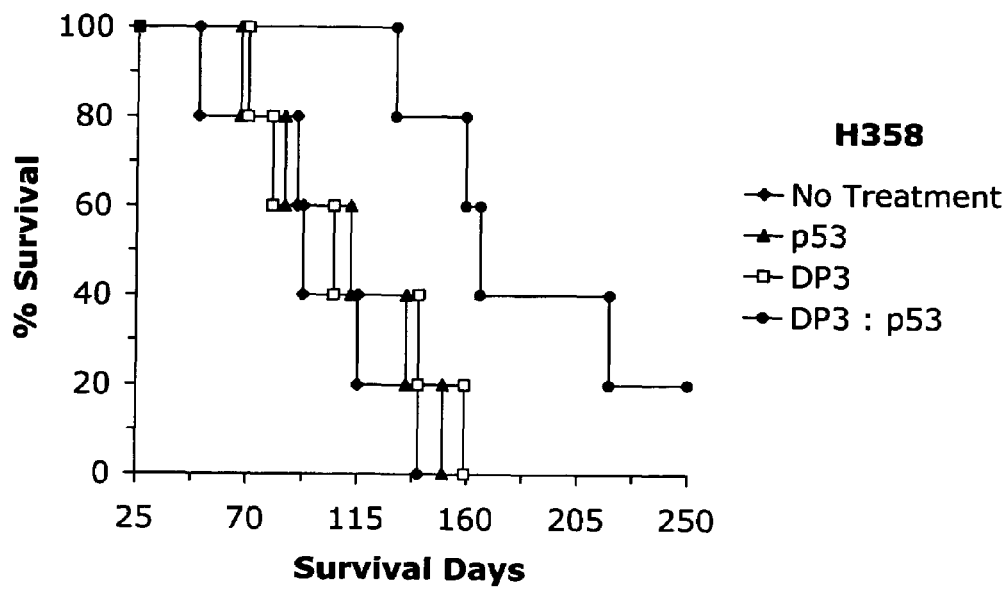
Figure 7D:
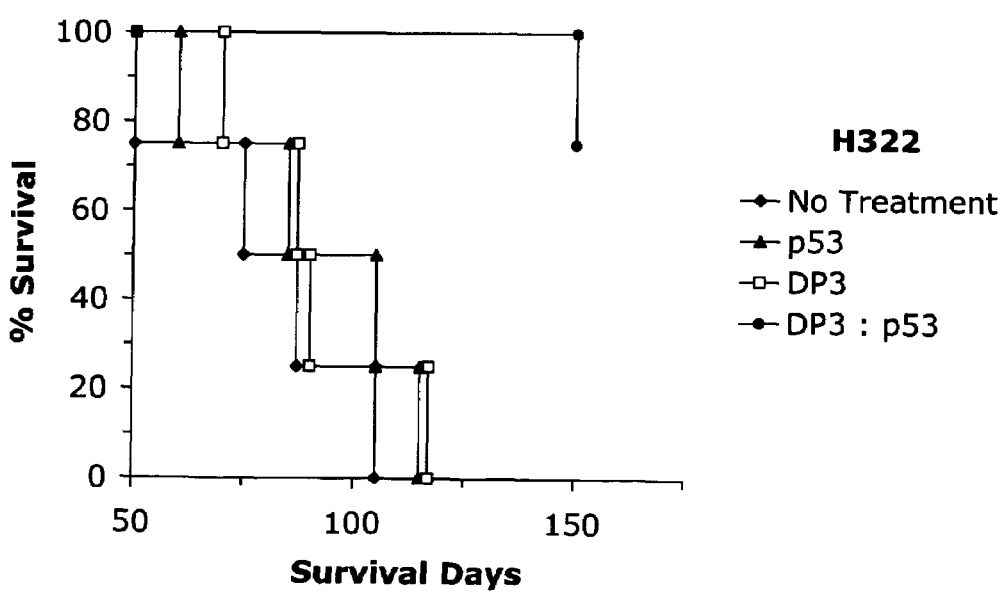

In the in vivo lung tumor growth inhibition experiments, male nu/nu mice were inoculated with $10^6$ H358 cells intratracheally and divided into 4 groups with 5 mice in each group. One group was untreated. The other three groups were treated intratracheally with pC53SN plasmid alone, DP3 liposomes alone, or DP3/p53 complex on days 4, 8, and 12 after H358 inoculation, respectively. The dose was 2 µg DNA/administration. On day 74, the lungs were resected and weighed (FIG. 6).

DP3/p53 resulted in a significant tumor growth inhibition effect: there were no visible tumors in the lung tissue, and all 5 mice in this group were alive on day 74. All three control groups (untreated, pC53SN alone, DP3 alone) showed complete replacement of lung parenchyma by tumors, and one mouse was sacrificed because of lung tumor burden in each of the three control groups before day 74. The average lung:body weight ratios of the three control groups was 6-fold to 13-fold higher than that of DP3/p53 treated group. There was no significant difference between the average lung:body weight ratios of DP3/p53 treated mice and normal mice without tumor inoculation (8.05 50 vs 7.28 mg/g, n=13, p>0.1).

Both p53 null (H358, p53 deletion) and p53 mutant (H322, p53 248 codon point mutation) tumor bearing mice were used in the survival experiments. In experiment 1, mice were inoculated with $2\times10^6$ H358 cells/mouse intratracheally, and the median survival of the three control groups (untreated, pC53SN alone, DP3 alone) was 92 days. In experiments 2 and 3, mice were inoculated with $1\times10^6$ H358 cells/mouse, and the median survivals of the three control groups were 106 and 110 days, respectively. In experiment 4, mice were inoculated with 1×10⁶H322 cells/mouse intratracheally, and the median survival of the three control groups was 80 days. The dose was 2 μg DNA/administration for experiment 1–3 and 8 μg DNA/administration for experiment 4.

The survival tests showed that after only five doses of DP3/p53 treatment, the average life span of the treated animals was more than doubled in all experiments (from 92–110 days to 175–202 days in experiments 1–3, p<0.007 by Log rank test; from 80 days to >180 days in experiment 4 p<0.008 by log rank test). DP3 alone or pC53SN plasmid alone had no significant effect (FIG. 7). Therefore, p53 delivered by the liposome system of the present invention effectively inhibited H358 or H322 lung tumor growth and prolonged the life span of tumor bearing mice by 2-fold with only five doses of treatment.

In this study, the delivery of the p53 gene to the bronchial epithelium was demonstrated using a liposome delivery system. This an effective approach to treat endo-bronchial malignancies in which overexpression of p53 causes cell death. Cationic liposome-p53 complex has been used intravenously to treat human breast cancer implanted in nude mice, but its efficacy was limited due to the fact that liver and serum components would destroy the vast majority of liposomes. Direct application of the liposome/gene complex to the surface of the target tissue should greatly enhance its delivering efficiency, hence its efficacy.

Liposomes can be administered directly onto the bronchial epithelium either intratracheally or through aerosol inhalation. Compared to intratracheal administration, aerosol inhalation is much easier and more amenable to multiple administration schedules, especially for human and large animals. Intratracheal administration was used in these experiments and the number of administrations was limited to a maximum of five because of the difficulties in performing repeated intratracheal administrations in mice. With aerosol inhalation, it is reasonable to expect better results in human or large animals simply because more doses can be administered. Liposomes have been used in aerosolized preparations with minimal toxicity and no immunogenicity (Canonnico, et al., *J. Appli. Physiol.* 77, 415–419 (1994); E. W. Alton et al., *Nat. Genet.* 5, 135–142 (1993)), and the feasibility of gene delivery by cationic liposomes through the airways, including by aerosol inhalation, has been demonstrated in mice, rats, and rabbits (Brigham et al., *Am. J. Med. Sci.* 298, 278–281 (1989); Canonico, et al., *Am. J. Respir. Cell Mol. Biol.* 10, 24–29 (1994); K. Yoshimura et al., *Nucleic. Acids Res.* 20:3233–3240, (1992); Alton et al., *Nat. Genet.* 5, 135–142 (1994); Stribling, et al., *Proc. Natl. Acad. Sci. USA.* 89,11277–11281 (1992); Hyde et al., *Nature* 362, 250–255 (1993); Hazinski, et al., *Am. J. Respir. Cell Mol. Biol.* 4, 206–210 (1991); Logan et al., *Gene Ther.* 2, 38–49 (1995).

Adenoviral and retroviral vectors have been used to deliver several genes into human tumors by intratumoral or regional administration, including the delivery of the p53 gene into lung cancer tumors (Rosenfeld et al., *Science* 252, 431–434 (1991); Flotte et al., *Proc. Natl. Acad. Sci. USA.* 90, 10613–10617 (1993); Hickman et al., *Hum. Gene Ther.* 5, 1477–1483 (1994); Zhang et al., *Hum.an Gene Ther.* 6, 155–164 (1995); Roth et al., *Nat. Med.* 2, 985–991 (1996). However, in the case of treating premalignancy and early lung cancer in the bronchial epithelium, cationic liposomes have distinct advantages over viral carriers. First, liposomes have minimal toxicity and no immunogenecity, and liposomes can be administered repeatedly. In contrast, viral carriers have shown significant toxicity and immunogenicity, which render their repeated use very difficult. Repeatable administration is important in this case because one administration of either liposome/gene or virus/gene particles may not penetrate deeply enough into the bronchial epithelium to reach all the dysplastic or malignant cells, even though the bronchial premalignant and malignant lesions are superficial and their thickness limited to a few layers of cells. With repeated administration, surface dysplastic or malignant cells are expected to be killed first and then deeper layers of abnormal cells are exposed and subsequently killed. Although liposome-mediated transfection is generally less efficient than adenoviral transfection, this disadvantage should be readily overcome by repeated administration. Second, liposomes can be delivered by aerosol inhalation, whereas aerosolized viral particles would represent a significant environmental biohazard by potentially infecting healthy individuals and therefore a less viable alternative.

In these experiments, the p53 killing efficiency was much higher than the transfection efficiency under the optimal transfection conditions for both H358 and H322 (containing p53 codon 248 point mutation) cell lines. The transfection efficiency measured by β-gal staining was about 10% for H358 and H322 cells. In contrast, the p53 killing efficiency were 30–40% for H358 and H322 cells, as evidenced by the cell survival test (FIG. 3) and in vivo results (FIG. 6 and FIG. 7). The possible reasons are that the transfection efficiency is actually much higher than that measured by β-gal staining since β-gal activity is not a sensitive method for measuring transfection efficiency and that a "bystander effect" may exist, as that observed previously with adenoviral/p53 transfection.

A variety of other genes such as rb, bax, p16 and chemotherapeutic agents such as cisplatin may also be delivered to the bronchi using the system of the present invention for the purpose of killing the bronchial premalignant and malignant cells before they invade deeply into the lung parenchyma. As molecular diagnostic techniques advance, the diagnosis and genetic characterization of bronchial premalignancy and early malignancy will become easier and more practical. With the combination of different genes and chemotherapeutic agents delivered using this system, the goal of greatly reducing human lung cancer occurrences and mortality may soon become reachable.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A nebulized liposome:DNA aerosol suitable for delivery of said DNA to the respiratory tract of an individual upon inhalation of said aerosol, comprising:
   (a) one of a cationic lipid dipalmitoyl-sn-glycero-ethylphosphocholine (DPEP) or dilauroyl-sn-glycero-ethylphosphocholine (DLEP) and dioleoylphosphatidylethanolamine (DOPE); and
   (b) a plasmid cDNA sequence encoding a protein having tumor suppressor or pro-apoptotic activity; wherein said cationic lipid and said plasmid cDNA are present in the composition in a ratio of about 2:1 μg lipid: μg DNA to about 24:1 μg lipid: μg DNA.

2. The liposome:DNA aerosol of claim 1, wherein one of the cationic lipids and dioleoylphosphatidylethanolamine are present in said liposome in a weight ratio of about 6:1 mg:mg to about 1:1 mg:mg.

3. The liposome:DNA aerosol of claim 1, wherein said liposome has a size of about 25 nm to about 1,500 nm.

4. The liposome:DNA aerosol of claim 3, wherein said liposome has a size of about 100 nm to about 500 nm.

5. The liposome:DNA aerosol of claim 1, wherein said plasmid cDNA encodes a protein having tumor suppressor activity selected from the group consisting of p53, p16, retinoblastoma and protein encoded by fragile histidine triad gene.

6. The liposome:DNA aerosol of claim 1, wherein said plasmid cDNA encodes a protein having pro-apoptotic activity selected from the group consisting of bax, bak and bad.

* * * * *